(12) United States Patent
Eidenschink et al.

(10) Patent No.: US 12,349,884 B2
(45) Date of Patent: Jul. 8, 2025

(54) DEVICES AND METHODS FOR THE TREATMENT OF VASCULAR ABNORMALITIES

(71) Applicant: St. Jude Medical, Cardiology Division, Inc., St. Paul, MN (US)

(72) Inventors: Tracee Eidenschink, Wayzata, MN (US); Andrea Stafford, New Brighton, MN (US); Brian J. Perszyk, Shoreview, MN (US); Erika A. Beek, Bloomington, MN (US); Michael Meyer, Minnetrista, MN (US); Pankaj Gupta, Maple Grove, MN (US); Philip Osterbauer, Wyoming, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 509 days.

(21) Appl. No.: 17/841,114

(22) Filed: Jun. 15, 2022

(65) Prior Publication Data
US 2022/0395266 A1 Dec. 15, 2022

Related U.S. Application Data

(60) Provisional application No. 63/210,854, filed on Jun. 15, 2021.

(51) Int. Cl.
*A61B 17/12* (2006.01)
*A61B 17/00* (2006.01)
*A61M 25/01* (2006.01)

(52) U.S. Cl.
CPC .... *A61B 17/0057* (2013.01); *A61B 17/00234* (2013.01); *A61M 25/0147* (2013.01);
(Continued)

(58) Field of Classification Search
CPC .......... A61B 17/0057; A61B 17/00234; A61B 2017/00004; A61B 2017/00243;
(Continued)

(56) References Cited

U.S. PATENT DOCUMENTS

| 4,917,089 A * | 4/1990 | Sideris ............... A61B 17/0057 606/153 |
| 5,334,217 A * | 8/1994 | Das .................... A61B 17/0057 606/151 |

(Continued)

FOREIGN PATENT DOCUMENTS

| WO | 9313712 A1 | 7/1993 |
| WO | 2004012603 A1 | 2/2004 |

(Continued)

OTHER PUBLICATIONS

European Search Report for EP Patent Application No. 22179129, mailed Oct. 20, 2022, 12 pages.

*Primary Examiner* — Ryan J. Severson
(74) *Attorney, Agent, or Firm* — Armstrong Teasdale LLP

(57) ABSTRACT

Described herein is a medical device including a frame having proximal and distal ends. The frame includes a proximal disc at the proximal end, a distal disc at the distal end, and a connecting segment extending between the proximal end and the distal end and connecting the proximal and distal discs. Each of the proximal and distal discs includes a respective plurality of lobes. Each lobe is defined by a peripheral strut. The medical device also includes at least one patch. The at least one patch is coupled to at least one of the proximal and distal discs of the frame.

20 Claims, 15 Drawing Sheets

(52) U.S. Cl.
CPC ............... *A61B 2017/00004* (2013.01); *A61B 2017/00243* (2013.01); *A61B 2017/00606* (2013.01); *A61B 2017/00623* (2013.01); *A61B 2017/00632* (2013.01); *A61B 2017/00867* (2013.01); *A61B 2017/12081* (2013.01)

(58) Field of Classification Search
CPC ........... A61B 2017/00606; A61B 2017/00623; A61B 2017/00632; A61B 2017/00867; A61B 2017/12081; A61B 2017/00575; A61B 2017/00592; A61M 25/0147
See application file for complete search history.

(56) References Cited

U.S. PATENT DOCUMENTS

| | | | | |
|---|---|---|---|---|
| 5,451,235 A | * | 9/1995 | Lock | A61B 17/0057 606/232 |
| 5,578,045 A | * | 11/1996 | Das | A61B 17/0057 604/95.01 |
| 6,171,329 B1 | * | 1/2001 | Shaw | A61B 17/0057 606/151 |
| 6,214,029 B1 | * | 4/2001 | Thill | A61B 17/0057 606/213 |
| 7,582,104 B2 | * | 9/2009 | Corcoran | A61B 17/0057 606/151 |
| 9,138,213 B2 | * | 9/2015 | Amin | A61B 17/12122 |
| 9,381,006 B2 | * | 7/2016 | Masters | A61B 17/0057 |
| 10,219,795 B2 | * | 3/2019 | Widmer | A61B 17/12122 |
| 10,265,059 B2 | * | 4/2019 | Rowe | A61F 2/2427 |
| 11,724,075 B2 | * | 8/2023 | Johnson | A61M 27/002 604/8 |
| 11,883,014 B2 | * | 1/2024 | Bloomquist | A61B 17/0057 |
| 2007/0066994 A1 | * | 3/2007 | Blaeser | A61B 17/0057 606/213 |
| 2008/0077180 A1 | | 3/2008 | Kladakis et al. | |
| 2012/0029556 A1 | * | 2/2012 | Masters | A61B 90/39 606/213 |
| 2012/0071918 A1 | * | 3/2012 | Amin | A61B 17/0057 606/213 |
| 2012/0143242 A1 | | 6/2012 | Masters | |
| 2012/0197292 A1 | * | 8/2012 | Chin-Chen | A61B 17/08 606/213 |
| 2013/0165967 A1 | | 6/2013 | Amin et al. | |
| 2016/0249898 A1 | | 9/2016 | Widmer et al. | |
| 2017/0224323 A1 | | 8/2017 | Rowe et al. | |
| 2020/0179663 A1 | | 6/2020 | McDaniel et al. | |
| 2022/0395266 A1 | * | 12/2022 | Eidenschink | A61B 17/00234 |

FOREIGN PATENT DOCUMENTS

| | | |
|---|---|---|
| WO | 2009137755 A1 | 11/2009 |
| WO | 2016087061 A1 | 6/2016 |
| WO | 2020018699 A1 | 1/2020 |

* cited by examiner

DEVICES AND METHODS FOR THE TREATMENT OF VASCULAR ABNORMALITIES

CROSS REFERENCE TO RELATED APPLICATIONS

This application claims the benefit of priority to U.S. Prov. Pat. App. No. 63/210,854 filed Jun. 15, 2021, which is incorporated by reference herein in its entirety.

BACKGROUND OF THE DISCLOSURE

A. Field of Disclosure

The present disclosure relates generally to medical devices that are used in the human body. In particular, the present disclosure is directed to embodiments of an occlusion device that enables subsequent crossing of the septal wall after the occlusion device is deployed thereat. More specifically, the present disclosure is directed to an occlusion device with a device frame having a plurality of lobes with at least one incorporated patch.

B. Background

An occluder is a medical device used to treat (e.g., occlude) tissue at a target site within the human body, such as an abnormality, a vessel, an organ, an opening, a chamber, a channel, a hole, a cavity, a lumen, or the like. For example, an occluder may be used in trans-catheter secundum atrial septal defect closures. Secundum atrial septal defects are common congenital heart defects that allow blood to flow between the left and right atria of the heart, decreasing cardiac output. Occluders may be employed to block this blood flow.

Percutaneous procedures are becoming more prevalent in surgical practice. At least some percutaneous procedures access the left atrium through the septal wall. Conventional devices for closing Atrial Septal Defects (ASD) include, for example, a braided-web closure device that is implanted in the septal wall, with braided-web discs on each side of the ASD that anchor the closure device. To cross the septal wall in a patient with previously closed ASD (e.g., to treat atrial fibrillation or place a Left Atrial Appendage closure device), a physician may need to navigate through the braided-web discs of the closure device.

Accordingly, it would be desirable to reduce the presence of the braided-web discs, while maintaining the fundamental function and effectiveness of an occluder for closing an ASD.

SUMMARY OF THE DISCLOSURE

The present disclosure is directed to a medical device. The medical device includes a frame having proximal and distal ends. The frame includes a proximal disc at the proximal end, a distal disc at the distal end, and a connecting segment extending between the proximal end and the distal end and connecting the proximal and distal discs. Each of the proximal and distal discs includes a respective plurality of lobes. Each lobe is defined by a peripheral strut. The medical device also includes at least one patch. The at least one patch is coupled to at least one of the proximal and distal discs of the frame.

The present disclosure is also directed to a delivery system for delivering a medical device to a target site. The delivery system includes a medical device including a frame having proximal and distal ends. The frame includes a proximal disc at the proximal end, a distal disc at the distal end, and a connecting segment extending between the proximal end and the distal end and connecting the proximal and distal discs. Each of the proximal and distal discs includes a respective plurality of lobes. Each lobe is defined by a peripheral strut. The medical device also includes at least one patch. The at least one patch is coupled to at least one of the proximal and distal discs of the frame. The delivery system also includes a delivery device coupled to the medical device, the delivery device including a catheter and a delivery cable, wherein the medical device is coupled to the delivery cable, and wherein the delivery cable is configured to be advanced through the catheter to deploy the medical device at the target site.

The present disclosure is further directed to a method for closing an Atrial Septal Defect (ASD). The method includes providing a medical device that includes a frame having proximal and distal ends. The frame includes a proximal disc at the proximal end, a distal disc at the distal end, and a connecting segment extending between the proximal end and the distal end and connecting the proximal and distal discs. Each of the proximal and distal discs includes a respective plurality of lobes. Each lobe is defined by a peripheral strut. The medical device also includes at least one patch. The at least one patch is coupled to at least one of the proximal and distal discs of the frame. The method includes advancing the medical device to the ASD using a delivery system including a catheter and a delivery cable, positioning the medical device relative to the ASD to occlude blood flow, and de-coupling the medical device from the delivery cable to deploy the medical device.

BRIEF DESCRIPTION OF THE DRAWINGS

Corresponding reference characters indicate corresponding parts throughout the several views of the drawings. It is understood that the Figures are not necessarily to scale.

DETAILED DESCRIPTION OF THE DISCLOSURE

Figure 1:
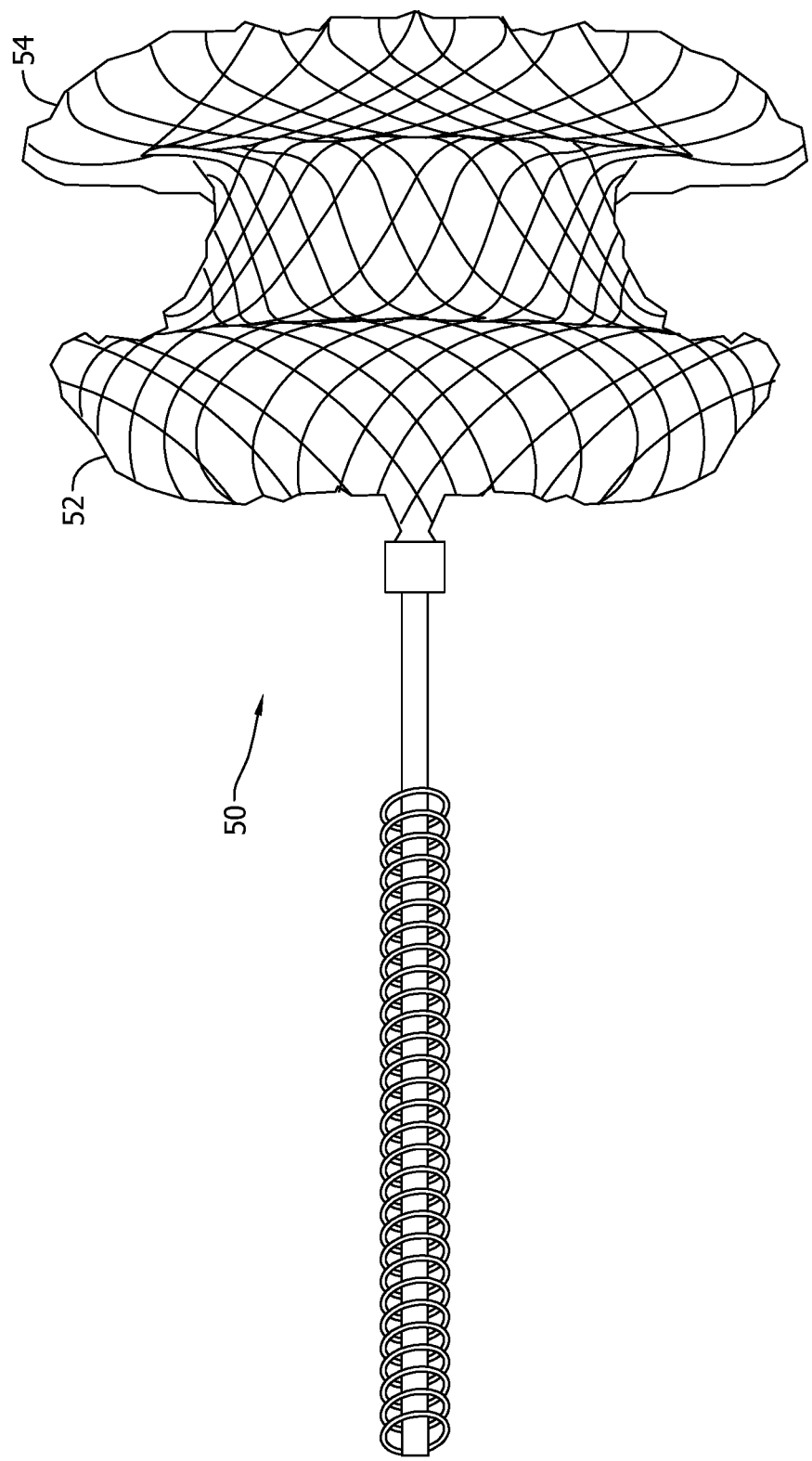
FIG. 1 illustrates a known medical device.

The present disclosure relates generally to medical devices that are used in the human body. Specifically, the present disclosure provides medical devices including occlusion devices having a frame including lobes and a patch. The patch may promote tissue ingrowth such that, after a period of time, the patch and tissue provide sufficient occlusion of the target site, without the need for braided-mesh discs. The occlusion devices of the present disclosure may reduce the delivery profile and minimize the amount of metallic material present in the device, compared to other known medical devices, which enables easier crossing of the atrial septal wall for future medical procedures once the device has been placed within the patient's body.

The disclosed embodiments may lead to more consistent and improved patient outcomes. It is contemplated, however, that the described features and methods of the present disclosure as described herein may be incorporated into any number of systems as would be appreciated by one of ordinary skill in the art based on the disclosure herein.

It is understood that the use of the term "target site" is not meant to be limiting, as the medical device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the medical device may be configured to bridge or otherwise support a variety of vascular abnormalities. For example, the vascular abnormality could be any abnormality that affects the shape of the native lumen, such as an atrial septal defect, an LAA, a lesion, a vessel dissection, or a tumor. Embodiments of the medical device may be useful, for example, for occluding an LAA, ASD, VSD, or PDA, as noted above. Furthermore, the term "lumen" is also not meant to be limiting, as the vascular abnormality may reside in a variety of locations within the vasculature, such as a vessel, an artery, a vein, a passageway, an organ, a cavity, or the like. For ease of explanation, the examples used herein refer to the occlusion of a septal defect (e.g., an atrial septal defect or ASD).

As used herein, the term "proximal" refers to a part of the medical device or the delivery device that is closest to the operator, and the term "distal" refers to a part of the medical device or the delivery device that is farther from the operator at any given time as the medical device is being delivered through the delivery device. In addition, the terms "deployed" and "implanted" may be used interchangeably herein.

Some embodiments of the present disclosure provide an improved percutaneous catheter directed intravascular occlusion device for use in the vasculature in patients' bodies, such as blood vessels, channels, lumens, a hole through tissue, cavities, and the like, such as an atrial septal defect. Other physiologic conditions in the body occur where it is also desirous to occlude a vessel or other passageway to prevent blood flow into or therethrough. These device embodiments may be used anywhere in the vasculature where the anatomical conditions are appropriate for the design.

The medical device may include one or more discs that are at least partially covered by a patch that acts as an occlusive material, while promoting native tissue growth, which is configured to substantially preclude or occlude the flow of blood. As used herein, "substantially preclude or occlude flow" shall mean, functionally, that blood flow may occur for a short time, but that the body's tissue growth to the biomaterial patch results in occlusion or flow stoppage after this initial time period.

The present disclosure now will be described more fully hereinafter with reference to the accompanying drawings, in which some, but not all embodiments of the disclosure are shown. Indeed, this disclosure may be embodied in many different forms and should not be construed as limited to the embodiments set forth herein; rather, these embodiments are provided so that this disclosure will satisfy applicable legal requirements. Like numbers refer to like elements throughout.

At least some conventional or known medical devices used for the occlusion of abnormalities, such as a medical device 50 shown in FIG. 1, include a proximal disc 52 and a distal disc 54, with a braided mesh configuration to facilitate thrombosis to seal a vascular abnormality. The collection of the thrombi in the mesh of the discs allows for the device to provide an occlusive effect. However, if the patient later requires a medical procedure that involves crossing over or through the implanted device, the physician must navigate through the braided material. This may increase the duration of a procedure and/or may adversely impact the sealing function of medical device 50, which may require an additional or extended procedure to implant a new medical device.

The medical devices of the present disclosure enable the closure and sealing of an abnormality while reducing the amount of metallic material implanted in the body, compared to known devices. Accordingly, the medical device of the present disclosure reduces or eliminates the above-described disadvantages of known medical devices while providing a sufficient closure and sealing effect.

Figure 2:
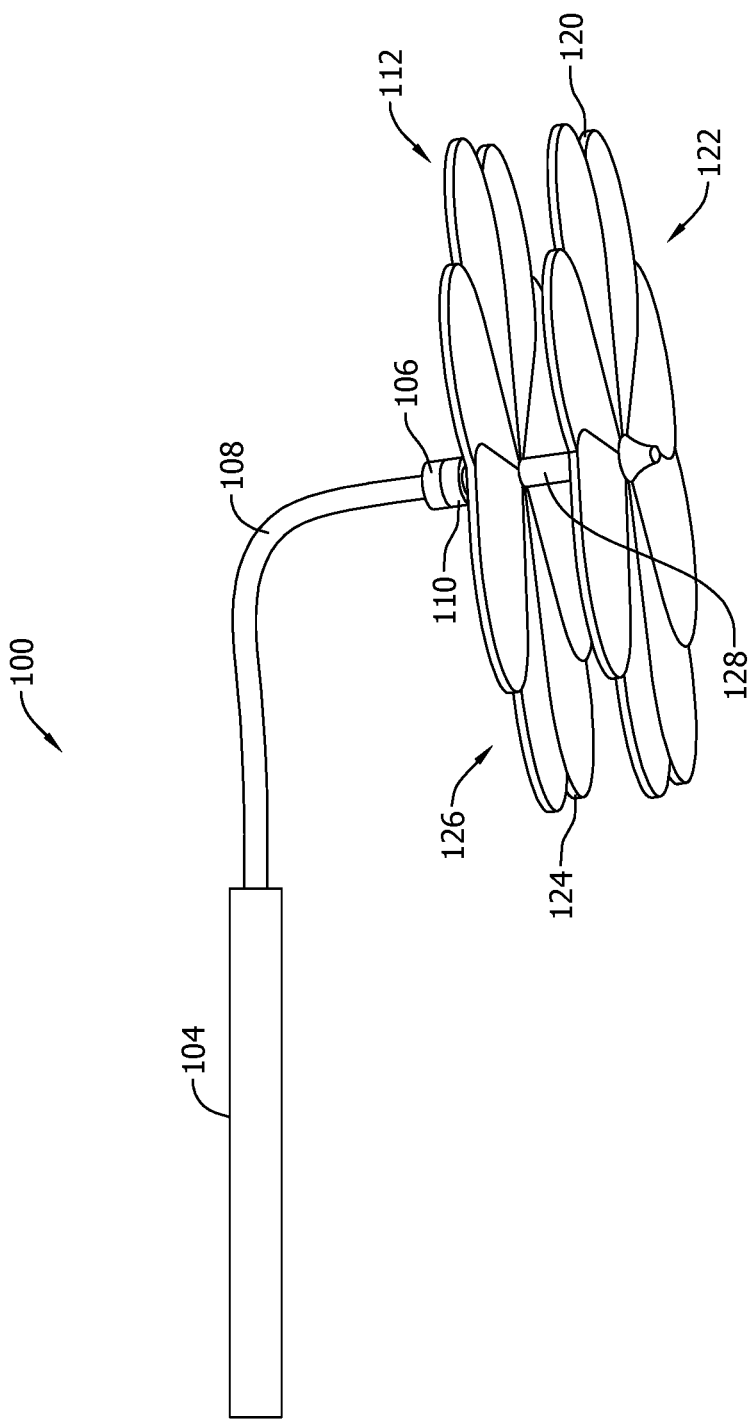
FIG. 2 is an exemplary embodiment of a delivery system including a delivery device and a medical device in accordance with the present disclosure.
Figure 3:
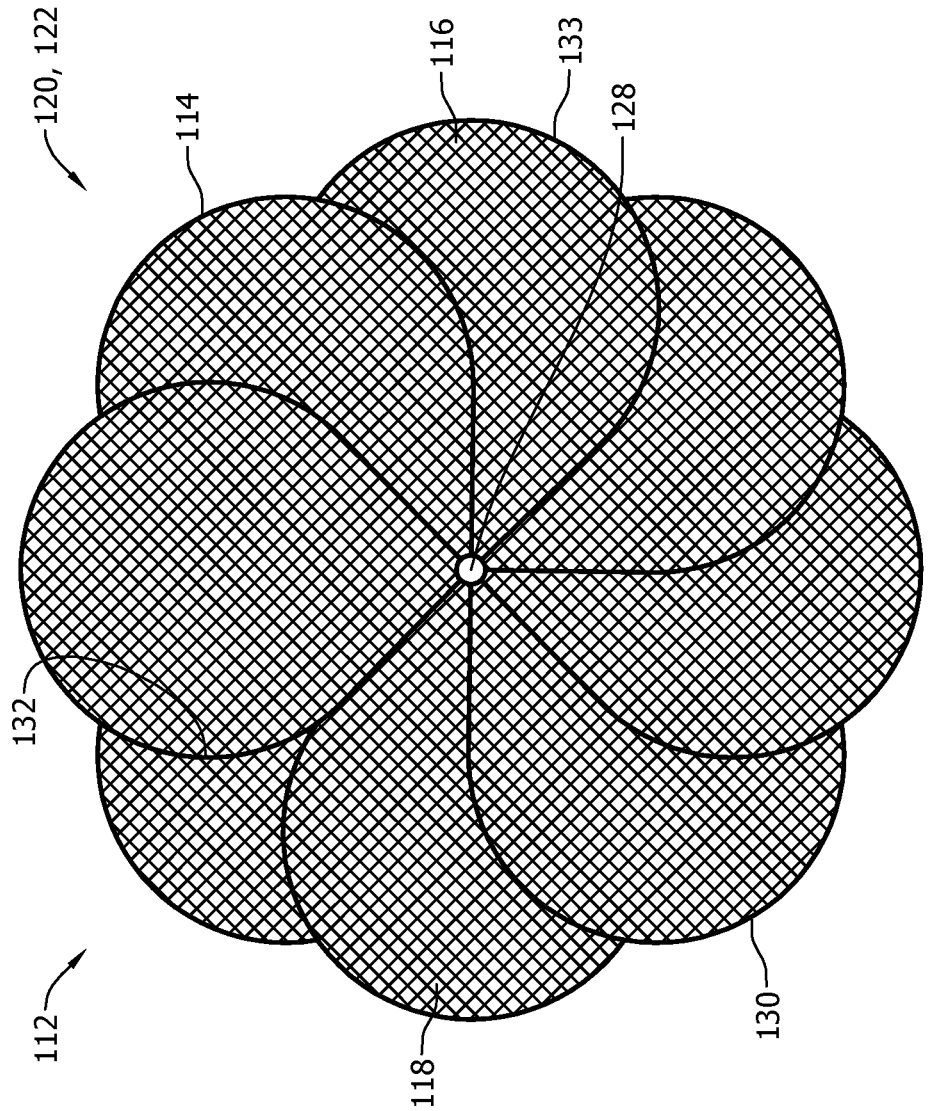
FIG. 3 illustrates a top sectional view of a first exemplary embodiment of the medical device including a frame and patch, in accordance with the present disclosure.
Figure 4:
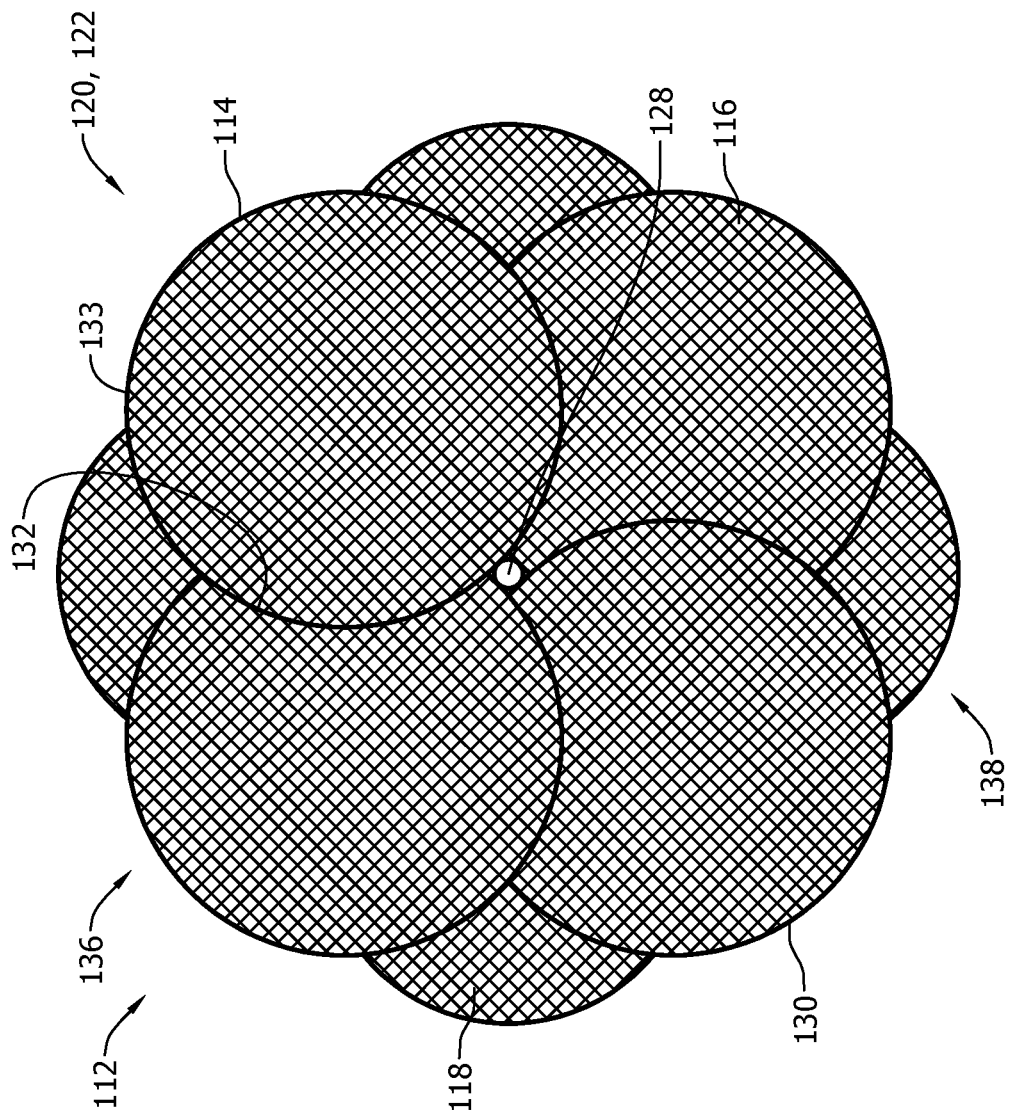
FIGS. 4 and 5 illustrate top sectional views of additional embodiments of the medical device in accordance with the present disclosure.
Figure 5:
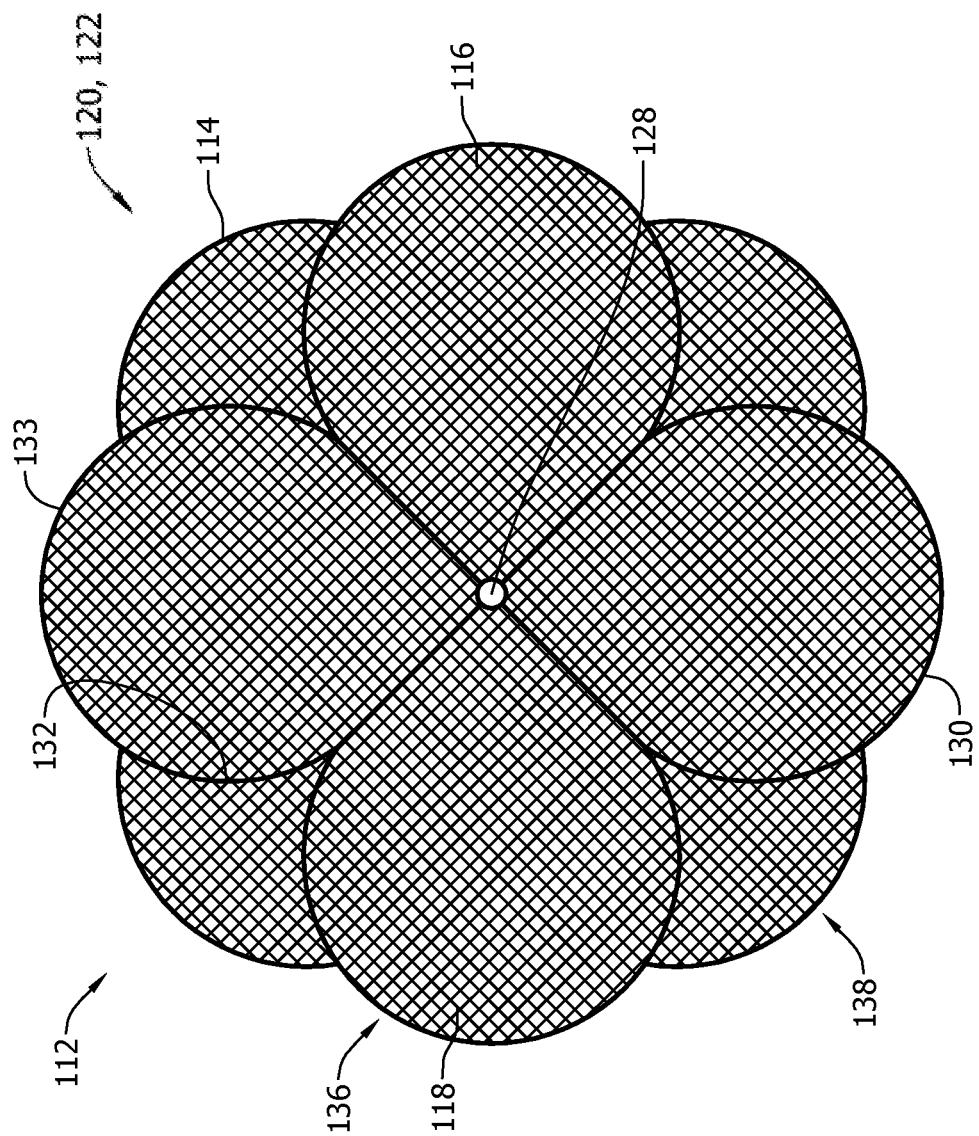

Turning now to FIG. 2, a schematic diagram of a delivery system 100 is shown. Delivery system 100 includes a catheter 104 and a coupling member 106 configured to couple a distal end of a delivery cable 108 to a connecting member 110 of a medical device 112 for facilitating the deployment of medical device 112 at a target site. Medical device 112 is deployed to treat the target site, and, in the example embodiment, is an occlusion device ("occluder"). FIGS. 3-5 illustrate top sectional views of various embodiments of medical device 112. Specifically, with reference first to FIG. 3, medical device 112 includes a device frame 114 and at least one patch 116. Device frame 114 includes a plurality of lobes 118 that collectively define a distal disc 120, and distal disc 120 at least partially defines a distal end 122 of medical device 112. Although not shown in FIGS. 3-5, device frame 114 includes a proximal disc 124 (see FIG. 2) that at least partially defines a proximal end 126 of medical device 112 and frame 114. Proximal disc 124 is substantially the same as distal disc 120—that is, the foregoing and following description of distal disc 120 also apply to proximal disc 124. Proximal and distal discs 124, 120 are joined together by a connecting segment 128. In the exemplary embodiment, connecting segment 128 is coaxial with proximal and distal discs 124, 120. In other embodiments, connecting segment 128 is other than coaxial with (e.g., off-center with respect to) proximal disc 124 and/or distal disc 120.

Each lobe 118 extends outwardly from connecting segment 128 to an exterior edge 130, thereby defining a loop 132. In the exemplary embodiment, each lobe 118 is substantially similar to each other lobe 118 in distal disc 120. Alternatively, one or more lobes 118 is different from the other lobes 118 in distal disc 120. Each lobe 118 has a shape, size, and orientation defined by a respective strut 133. Struts 133 define the peripheral edges of lobes 118, and therefore may be referred to as "peripheral struts." In an exemplary embodiment, lobe 118 may have a substantially teardrop configuration (see FIGS. 3 and 5). In another embodiment, lobe 118 may have a substantially circular configuration (see FIG. 4). The shape of lobes 118 may be defined by a mold (e.g., by heat-setting the frame into a desired configuration to shape lobes 118 and/or the disc 120/124 formed thereby).

In the exemplary embodiment, lobes 118 are present in a planar, overlapped configuration. It is contemplated that lobes 118 may be arranged in many different configurations, limited only by the ability of the lobes 118 to form the respective disc and provide a suitable sealing effect for the device to effectively function as an occlusion device. For example, lobes 118 may have various shapes, sizes, relative positions without departing from the scope of the present disclosure. Moreover, each disc 120, 124 may be defined by any suitable number of lobes 118, including, for example, four, five, six, seven, eight, nine, ten, or more lobes.

In some embodiments, each of proximal and distal discs 124, 120 is an individual unitary component, each integrally formed by a single set of lobes 118. For example, each disc 120, 124 may be formed from a respective single, continuous wire that includes all struts 133 shaped to form all lobes 118 of the respective disc 120/124. Such a wire may be formed from any suitable material (e.g., a shape-memory metallic alloy, an elastic shape-memory or non-shape memory polymeric material, etc.). In other embodiments, as described further herein, frame 114 is a single tubular member that is cut and shaped to define lobes 118 and form discs 120/124. Alternatively, one or more lobes 118 may be separately formed and coupled together to define a disc 120/124 (e.g., lobes 118 may be connected to connecting segment 128 and/or to an alternative connecting mechanism).

In some embodiments, as shown in FIGS. 4 and 5, proximal and distal discs 124, 120 are each respectively formed from a first lobe layer 136 ("first layer" 136) and a second lobe layer 138 ("second layer" 138). First layer 136 is exterior to and overlaps second layer 138. First and second layers 136, 138 are coupled together by a connector, which may form part of connecting segment 128. This connector secures first and second layers 136, 138 in the offset position in which lobes 118 of first layer 136 are offset or staggered relative to lobes 118 of second layer 138.

In the exemplary embodiment, medical device 112 is delivered to the target site (e.g., using delivery system 100) in a constricted configuration, as described herein, through delivery catheter 104. Once at the target site, medical device 112 is advanced distally from delivery catheter 104, and expands or transitions from the constricted configuration to an expanded configuration when deployed at the target site. As described further herein, medical device 112 transitions from the constricted configuration to the expanded configuration in response to an axially compressive force (e.g., exerted by the shape memory material of frame 114).

Connecting segment 128 may be formed from a wire or tubular member. The wire of connecting segment 128 may be the same as a wire forming struts 133 that define lobes 118. It is contemplated that connecting segment 128 may be formed separate from struts 133 (from a same or different material). Alternatively, connecting segment 128 may be formed by a tubular member integral to a tubular member forming discs 124, 120 or coupled thereto. In other embodiments, connecting segment 128 is one or more threads (e.g., monofilament or multifilament thread/suture), elastic (e.g., polyurethane, tecothane, chronoprene), and/or other material (e.g., PET, KEVLAR™) coupling discs 120, 124 together. Additionally or alternatively, discs 120, 124 may be connected to connecting segment 128 via a ball-and-socket or swaged connection. It is contemplated that connecting segment 128 may be of various materials and configurations, limited only by the ability of the connecting segment (or other connecting component(s)) to connect proximal disc 124 and distal disc 120.

Patch 116, in the embodiments of FIGS. 3-5, is formed from separate patches, wherein each patch engages with or is coupled to a strut 133 of a respective lobe 118. Alternatively, patch 116 may be a unitary component that is stitched (or otherwise coupled) to each lobe 118 forming disc 120/124 at least around exterior edge 130. In some such embodiments, patch 116 is configured to surround proximal disc 124, distal disc 120, and at least a portion of connecting segment 128. When patch 116 is a unitary component, the portion of patch 116 surrounding connecting segment 128 is configured to fill an entire cavity defined by the vascular abnormality, for example, to form a plug.

In the exemplary embodiment, each patch 116 is coupled to the respective lobe 118 by sutures. In some such embodiments, a whipstitch is used to couple patch 116 to lobe 118. Additionally or alternatively, frame 114 includes multiple small indentations (not shown) configured to retain the suture material therein. In other embodiments, patch 116 is adhered to frame 114 (e.g., to a strut 133 of a respective lobe 118). Alternatively, the material forming the patch 116 may be dip coated or spray coated onto frame 114.

In the exemplary embodiment, connecting member 110 (see FIG. 2) is coupled to and extends from a proximal end of connecting segment 128 of medical device 112. Alternatively, connecting member 110 may be coupled to and extend from proximal disc 124. In the exemplary embodiment, connecting member 110 is an end screw. In other embodiment, the connecting member is implemented as one or more detents configured to be engaged by a corresponding component of the delivery device, as a ball-and-socket type connection, or as a snare-type connection. It is contemplated that connecting member 110 may be in a number of configurations limited only by the ability of the connecting member to effectively connect the medical device to the delivery cable and allow for the deployment of the medical device.

Figure 6:
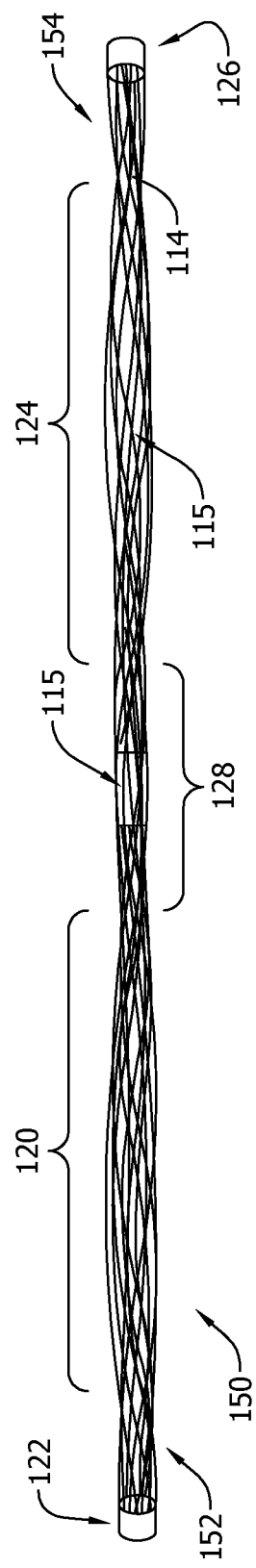
FIG. 6 depicts one exemplary embodiment of a medical device in accordance with the present disclosure in an initial configuration.
Figure 7:
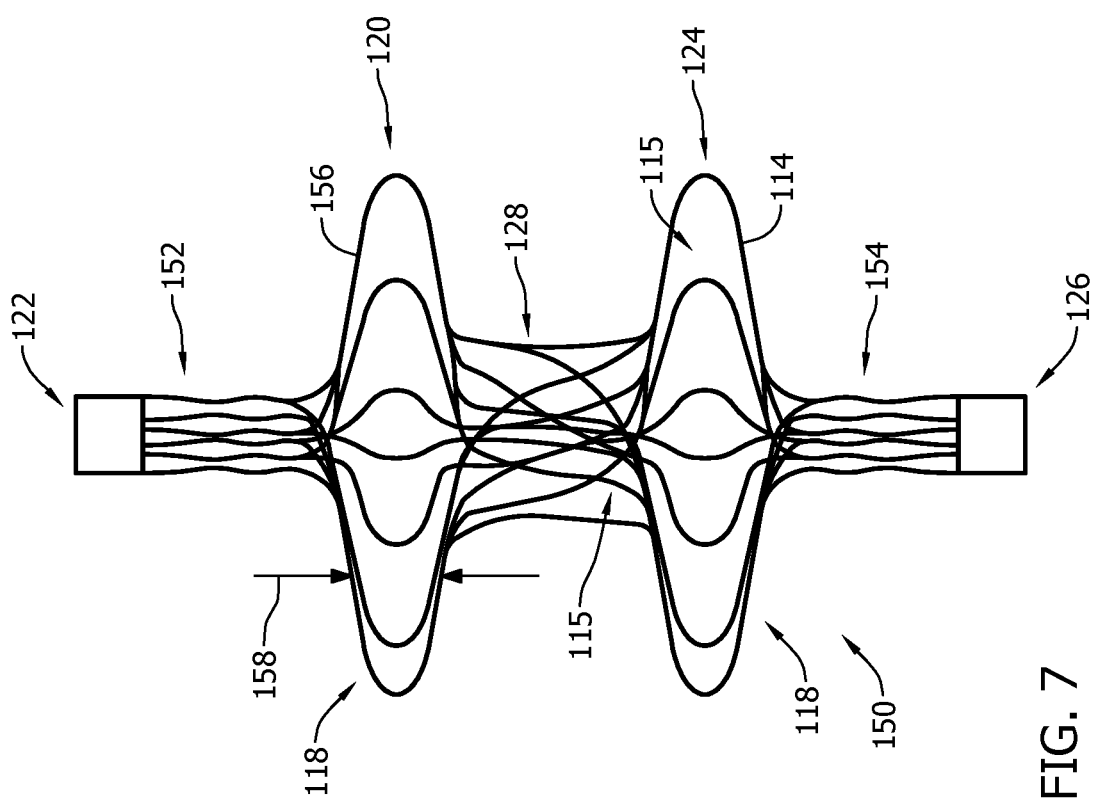
FIG. 7 is a side view of the medical device shown in FIG. 6 in an expanded configuration.
Figure 8:
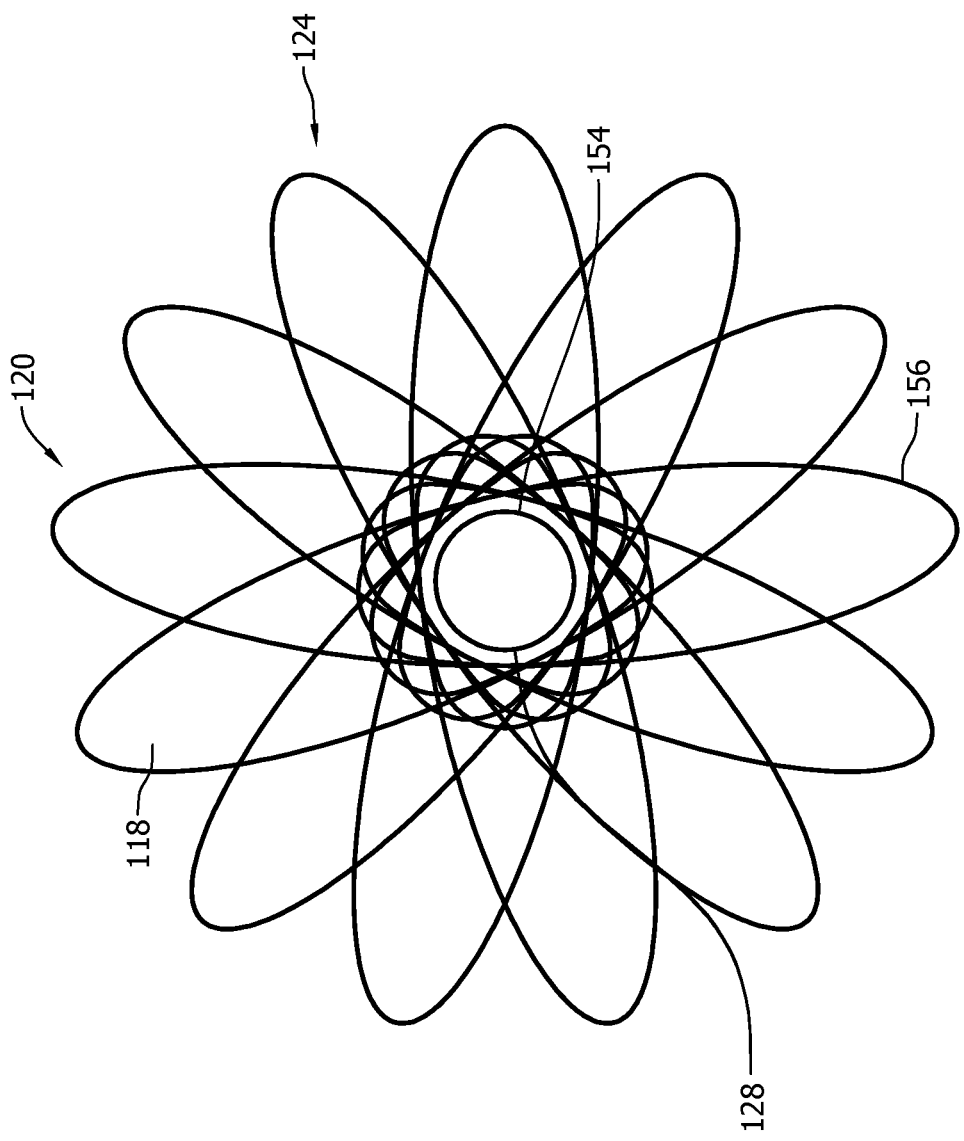
FIG. 8 is a top view of the medical device shown in FIG. 6 in the expanded configuration.

FIGS. 6-8 depict another exemplary embodiment of medical device 112, referred to as medical device 150. More specifically, FIG. 6 depicts medical device 150 in a constricted configuration, and FIGS. 7 and 8 are a side and top view, respectively, of medical device 150 in an expanded configuration. In this embodiment, frame 114 of medical device 150 is a laser-cut tubular frame 114. That is, frame 114 is one unitary component, and the particular shape and orientation of discs 120, 124 and connecting segment 128 are dependent upon the particular pattern of laser cutting forming frame 114. In the embodiment of FIGS. 6-8, frame 114 also defines a distal portion 152 and a proximal portion 154 of medical device 150, as described further herein.

Figure 11:
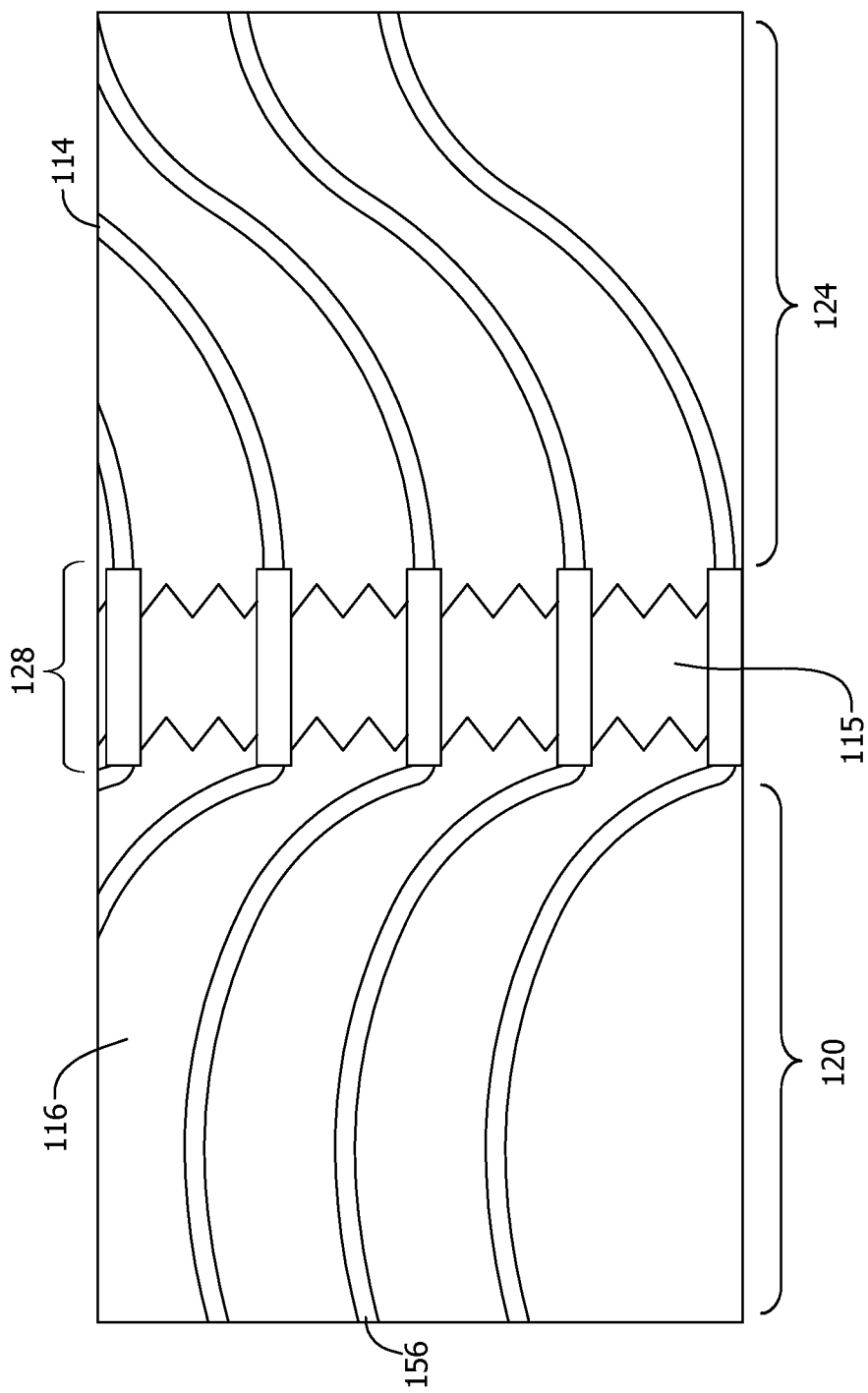
FIG. 11 is a schematic side view of a laser-cut medical device in an initial configuration.

The relative diameter of discs 120, 124 and connecting segment 128 is defined in part by the pattern of the laser cut. For example, smaller "cells" 115 of frame 114 (e.g., cells 115 of connecting segment 128 in the embodiment of FIGS. 6-8) result in a relatively smaller amount of expansion, whereas larger cells 115 (e.g., cells 115 of discs 120, 124 in the embodiment of FIGS. 6-8) result in a relatively larger amount of expansion. Accordingly, discs 120, 124 have a larger diameter than connecting segment 128. FIG. 11 depicts another embodiment of a laser-cut frame 114 cut from a sheet of material (e.g., a shape memory material, an elastic shape-memory or non-shape memory polymeric material, etc.) and including material that forms patch 116 coupled between adjacent struts 156. In these embodiments, connecting segment 128 expands when deployed, which enables improved centering of medical device 150 within the defect at the target site. In some alternative embodiments, connecting segment 128 may include no cells 115; that is, frame 114 may include a solid tubular structure corresponding to connecting segment 128. In such embodiments, connecting segment 128 may not expand or may expand by only a small amount.

In some embodiments, medical device frame 114 (e.g., a laser-cut tubular frame 114) is formed from a shape-memory material that tends to return to a pre-set expanded configuration (e.g., a heat-set expanded configuration) in the absence of a tensile axial force. In other embodiments, medical device 150 may have an initial non-expanded configuration corresponding to the configuration of the initially laser-cut tubular structure frame 114, and a compressive axial force may be required to transition medical device 150 to the expanded configuration. Medical device 150 may be configured to retain its shape in the expanded configuration once the compressive axial force is removed. In some such embodiments, medical device 150 may be heat-set in the expanded configuration after being compressed into the expanded configuration for the first time.

Turning to FIG. 7, for example, medical device 150 is shown in the expanded configuration. Frame 114 expands to define the expanded configuration of discs 120, 124 and connecting segment 128. In this embodiment, each lobe 118 is defined by a respective spiral strut 156. For lobes 118 forming proximal disc 124, struts 156 extend distally from proximal portion 154 in a spiral or helix configuration to connecting segment 128. For lobes forming distal disc 120, struts 156 extend distally from connecting segment 128 in a spiral or helix configuration to distal portion 152.

The amount of "spiral" of each strut 156 defines the resulting shape of the respective lobe 118. In the exemplary embodiment, each strut 156 terminates at about 320° to about 400° from where it originates (e.g., about 360°). That is, for the lobes 118 of proximal disc 124, the strut 156 spirals from proximal portion 154 to connecting segment 128 by about 320 to about 400° (e.g., about 360°); for the lobes 118 of distal disc 120, the strut 156 spirals from connecting segment 128 to distal portion 152 by about 320 to about 400° (e.g., about 360°).

Figure 9:
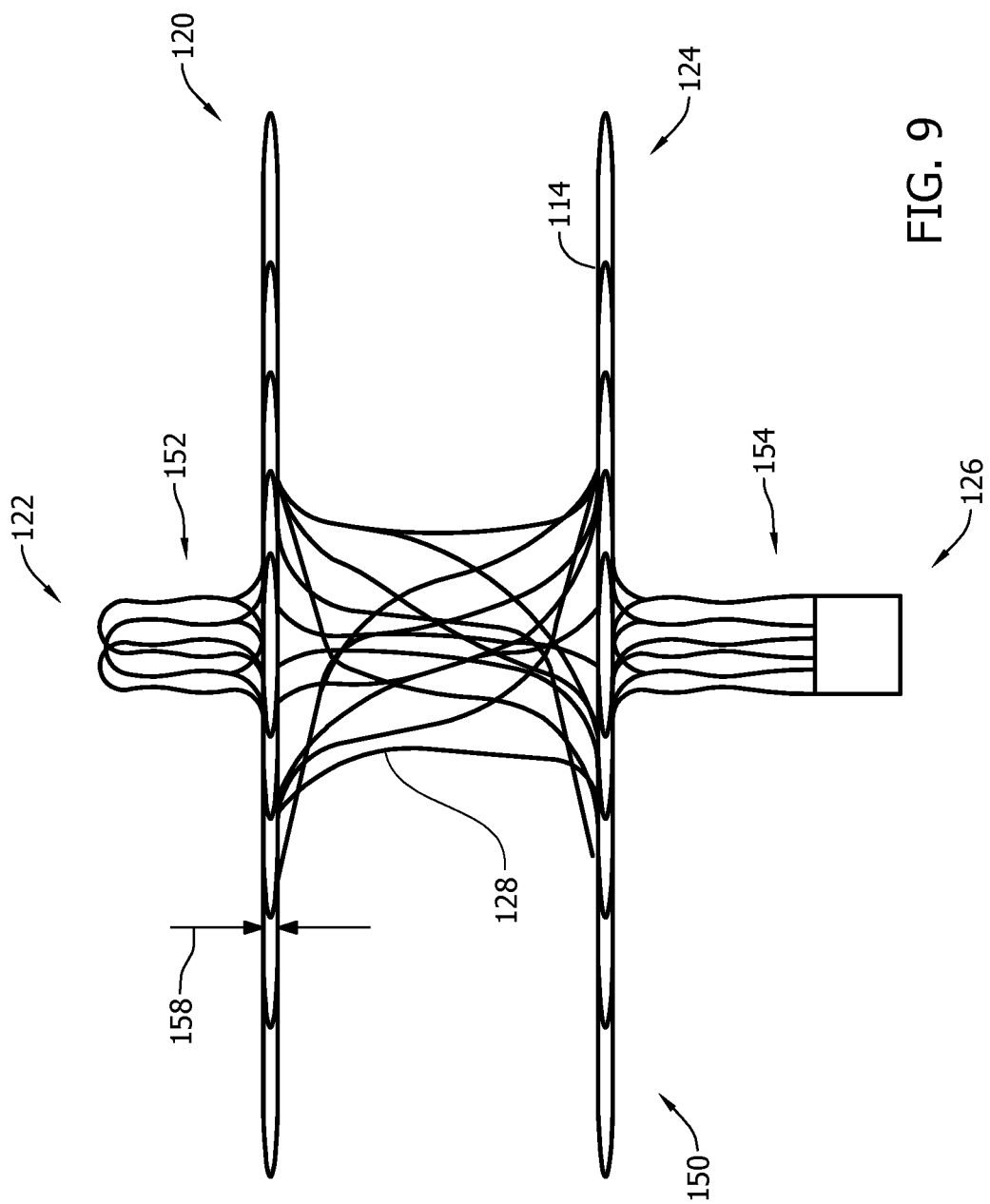
FIG. 9 is a side view of an alternative embodiment of the medical device shown in FIG. 6 in an expanded configuration.
Figure 14:
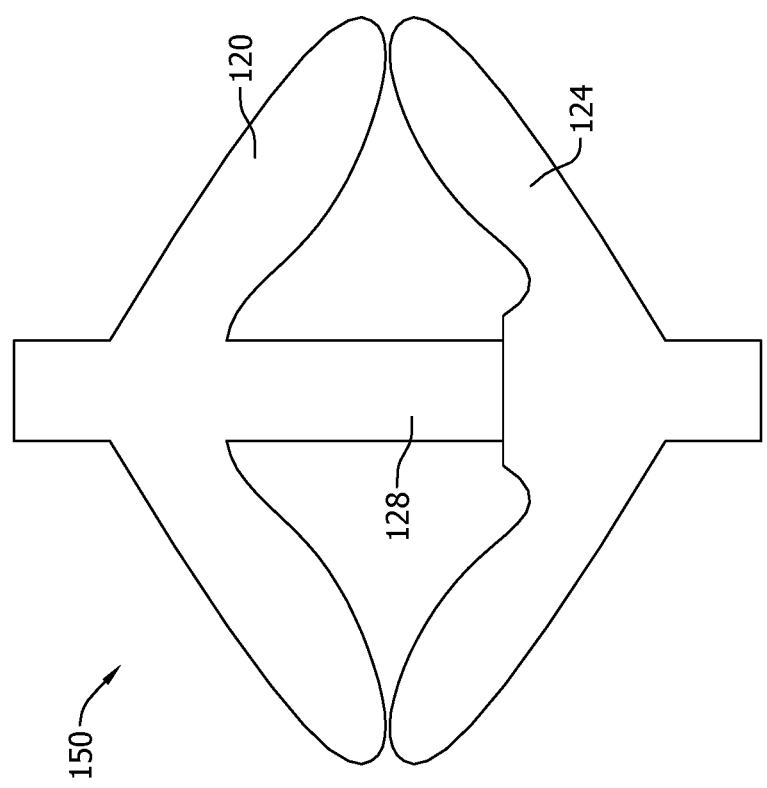
FIG. 14 is a side view of an alternative embodiment of the medical device in an expanded configuration.

In this embodiment, each lobe 118 has a depth 158, corresponding generally to a depth of the disc 120/124 formed from lobes 118. Depth 158 may be selectively determined according to one or more factors, such as an amount of spiral of struts 156, an amount of compressive force applied to frame 114, a size (e.g., a longitudinal length or circumferential width) of cells 115, and/or a selected profile defined during heat-setting of frame 114. For example, FIG. 9 depicts another embodiment of medical device 150 in the expanded configuration, in which discs 120, 124 have been heat-set with a reduced depth 158. Other characteristics of lobes 118 and/or discs 120/124 formed therefrom may be determined by laser-cut pattern of frame 114 and/or the heat-setting of frame 114 into the expanded configuration. For example, as shown in FIG. 14, discs 120/124 may be heat-set with an angled and/or concave shape. More specifically, in this embodiment, discs 120 and 124 are angled inwardly towards connecting segment 128, which may improve engagement with adjacent tissue (e.g., atrial walls) when medical device 150 is deployed. In other embodiments, discs 120 and 124 may be heat-set with any other shape (e.g., a concave or "cupped" shape) or any other relative orientation.

It should be understood that although discs 120 and 124 have been described as being substantially similar, any aspect of proximal disc 124 may differ from any aspect of distal disc 120 without departing from the scope of the present disclosure. For example, proximal disc 124 may differ from distal disc 120 according to any of the following aspects: more or fewer lobes 118, greater or reduced diameter, greater or reduced depth 158, or more or less spiral of struts 156 defining lobes 118.

Figure 10:
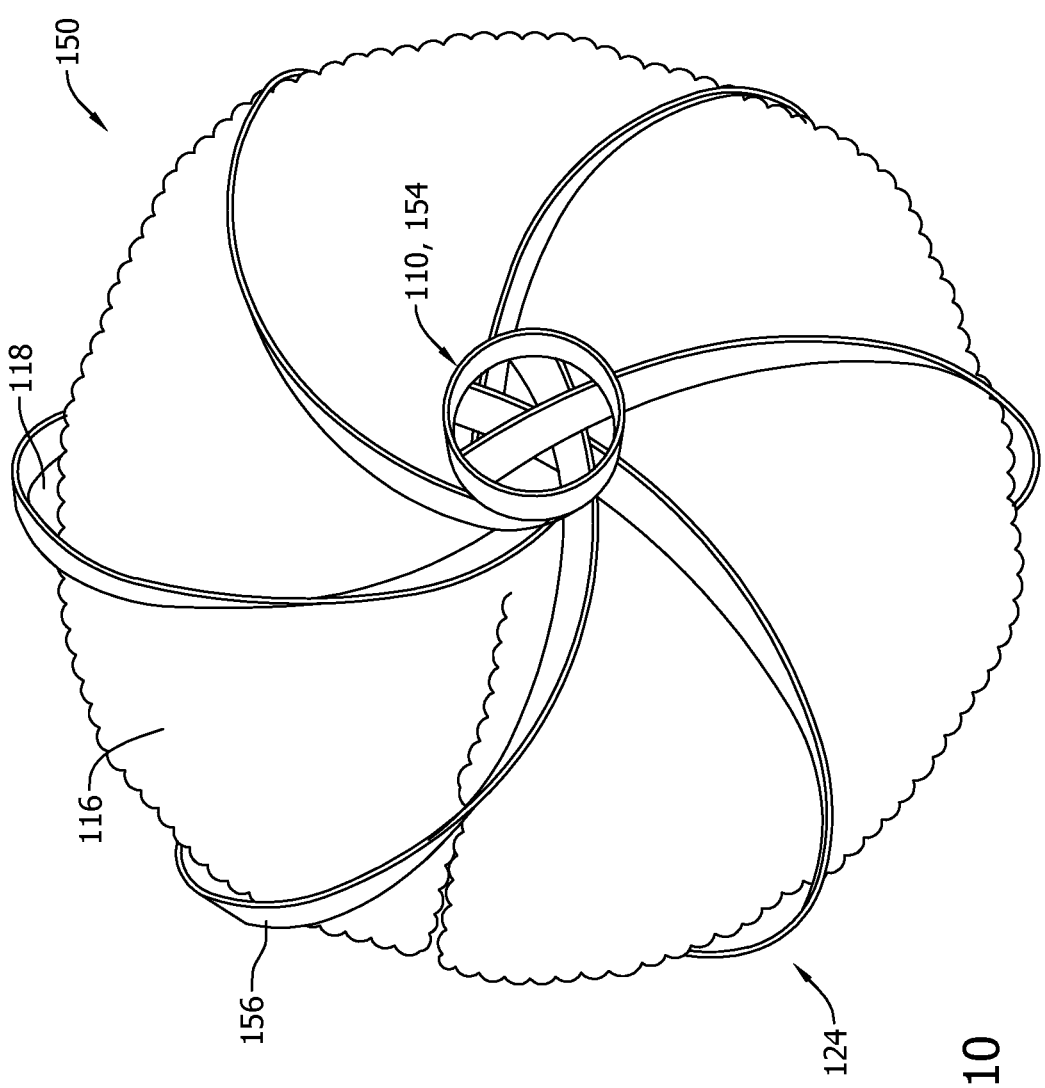
FIG. 10 is a top view of the medical device shown in FIGS. 6-8 including a patch.

FIG. 10 depicts medical device 150 including patch 116 positioned within proximal disc 124. As described above, patch 116 may be coupled to lobes 118 (e.g., to struts 156) by sutures, adhesives, or any other suitable coupling means. In this embodiment, patch 116 is a single, unitary patch 116, embodied as an occlusive fabric patch. Patch 116 is positioned within proximal disc 124 and is oriented transverse to depth 158 of proximal disc 124. A similar patch 116 may be similarly positioned within distal disc 120.

With reference to FIGS. 6-10, medical device 150 includes proximal portion 154 and distal portion 152. Proximal portion 154 extends proximally from proximal disc 124 and generally defines proximal end 126 of medical device 150. Distal portion 152 extends distally from distal disc 120 and generally defines distal end 122 of medical device 150. In some embodiments, proximal portion 154 includes connecting member 110, such as a threaded portion (not shown), which may be configured to couple to delivery cable 108 or a push wire (not shown). During deployment of medical device 150, medical device 150 is coupled to the distal end of delivery cable 108 via connecting member 110, and is advanced distally through delivery catheter 104 (see FIG. 4) to the target site. In some such embodiments, medical device 150 self-expands at the target site to occlude the target site.

In other embodiments, distal portion 152 includes an internally threaded endscrew (not shown) configured to couple to an externally threaded distal end (not shown) of delivery cable 108 or another delivery component, such as a pull wire. Delivery cable 108 (or the pull wire) extends through proximal portion 154 and longitudinally through medical device 150 (e.g., through discs 120, 124, connecting segment 128, and patch(s) 116) to couple to distal portion 152. In these embodiments, medical device 150, once deployed at the target site, is axially compressed by pulling distal portion 152 proximally while stabilizing proximal portion 154, as described further herein.

Figure 12:
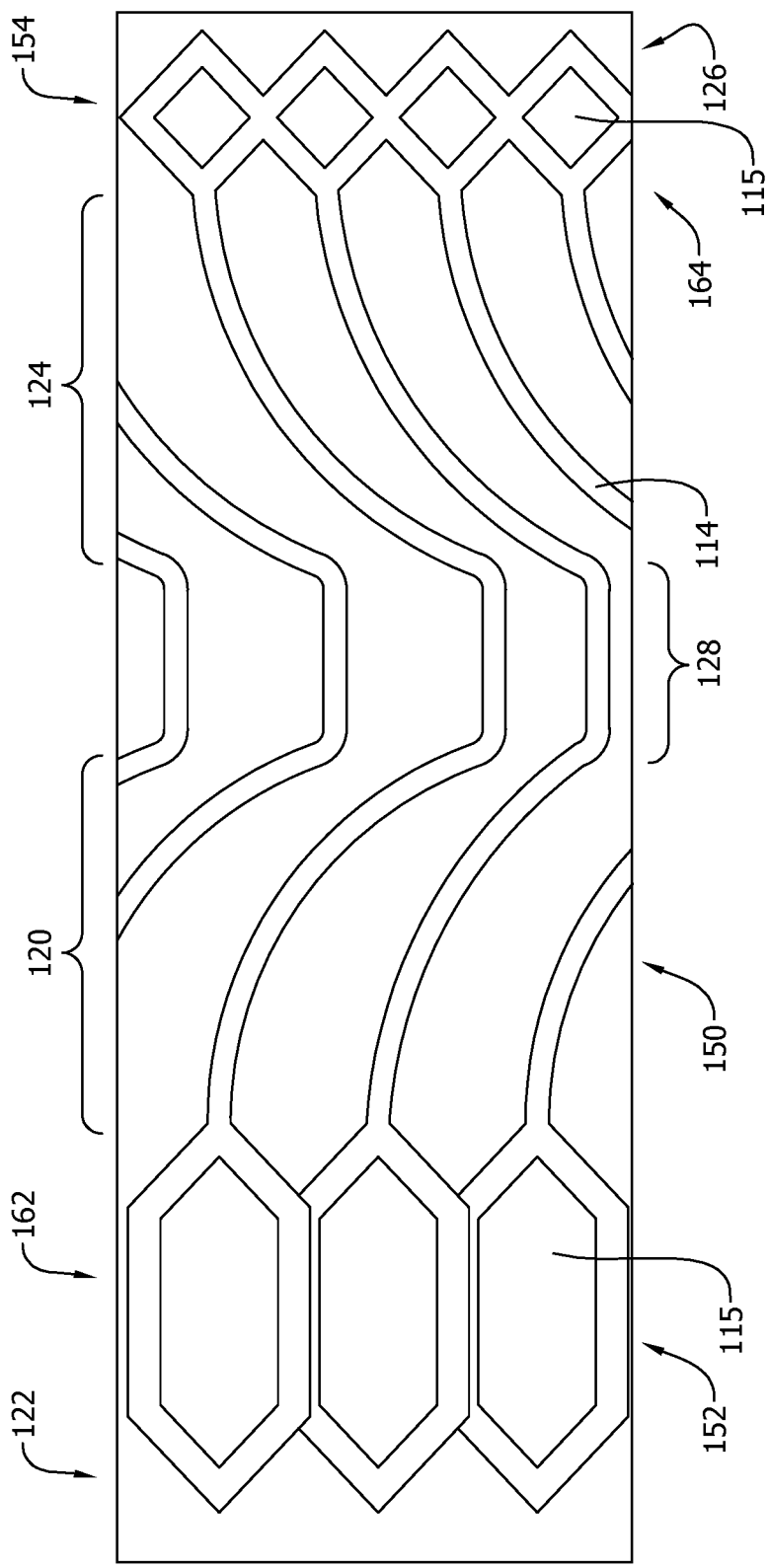
FIGS. 12 and 13 are side views of another laser-cut medical device in an initial, constricted configuration and an expanded configuration, respectively.
Figure 13:
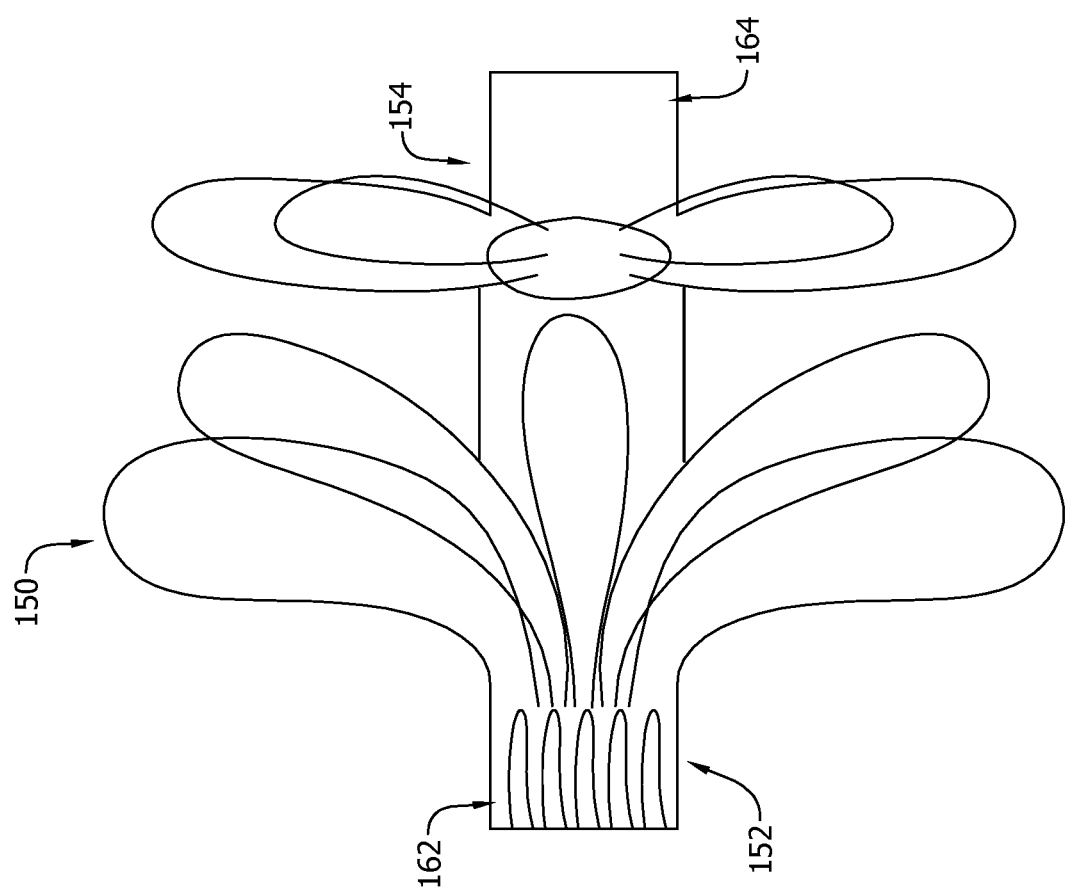

In some alternative embodiments, proximal portion 154 and/or distal portion 152 includes additional laser-cut features that facilitate deployment of medical device 150. Turning to FIGS. 12 and 13, an alternative embodiment of medical device 150 is shown, in which frame 114 includes distal portion (or "hub") 152 having distal end features 162 and proximal portion (or "hub") 154 having proximal end features 164. End features 162, 164 are implemented as cells 115 of the same tubular member of device frame 114. In some embodiments, connecting member 128 and/or end features 162, 164 are initially formed from the tubular member with a same diameter as the portions of the tubular member forming the discs 120, 124, and are able to be compressed (e.g., via crimping) for a smaller delivery profile.

In some embodiments, to deploy medical device 150, medical device 150 is delivered, using delivery system 100, to the target site in the initial or constricted configuration (see, e.g., FIG. 6). Delivery cable 108 or another sheath, push wire, or the like, is used to advance distal end 122 of medical device 150 out of catheter 104 until distal disc 120 is fully discharged from catheter 104. In some embodiments, medical device 150 is configured to expand to the expanded configuration without additional action, and distal disc 120 returns to its expanded configuration substantially immediately after exiting catheter 104.

In other embodiments, a compressive axial force is required to transition distal disc 120 to its expanded configuration. In such embodiments, delivery cable 108 or the pull wire coupled to distal portion 152 is retracted or pulled proximally, while delivery cable 108 or the push wire coupled to proximal portion 154 is stabilized, such that distal portion 152 is pulled proximally, thereby expanding distal disc 120 to its expanded configuration. In these embodiments, the push/pull components or wires may be implemented as separate wires that are independently controllable. One such component may be delivery cable 108. Alternatively, both push/pull components may be embodied as independently operable wires within delivery cable 108.

Thereafter, catheter 104 is retracted until proximal disc 124 is fully deployed. In some embodiments, medical device 150 is configured to expand to the expanded configuration without additional action, and proximal disc 124 returns to its expanded configuration substantially immediately after exiting catheter 104. In other embodiments, a compressive axial force is required to transition proximal disc 124 to its expanded configuration. In such embodiments, delivery cable 108 or the pull wire coupled to distal portion 152 is stabilized, while delivery cable 108 or the push wire coupled to proximal portion 154 is advanced distally, such that proximal portion 154 is pushed distally, thereby expanding proximal disc 124 to its expanded configuration. Discs 120, 124 may be maintained in the expanded position using any suitable means, including attaching an internal wire or cable, which extends through connecting segment 128, to expanded discs 120, 124. This wire may include the pull wire, described above, used to expand distal disc 120.

In one embodiment, device frame 114 is formed from a shape-memory material. One particular shape memory material that may be used is Nitinol. Nitinol alloys are highly elastic and are said to be "superelastic," or "pseudoelastic." This elasticity may allow medical device 112 to be resilient and return to a preset, expanded configuration for deployment following passage in a distorted form through delivery catheter 104. Further examples of materials and manufacturing methods for medical devices with shape memory properties are provided in U.S. Publication No. 2007/0265656 titled "Multi-layer Braided Structures for Occluding Vascular Defects" and filed on Jun. 21, 2007, which is incorporated by reference herein in its entirety.

It is also understood that device frame 114 may be formed from various materials other than Nitinol that have elastic properties, such as stainless steel, trade named alloys such as Elgiloy®, or Hastalloy, Phynox®, MP35N, FE35MN, Magnesium-RE alloys, CoCrMo alloys, metal, polymers, or a mixture of metal(s) and polymer(s). Suitable polymers may include PET (Dacron™), polyester, polypropylene, polyethylene, HDPE, Pebax™, nylon, polyurethane, silicone, PTFE, polyolefins and ePTFE. Additionally, it is contemplated that the device frame may comprise any material that has the desired elastic properties to ensure that the device may be deployed and function as an occluder in a manner disclosed within this application. It is also understood that device frame 114 may be formed from various materials other than materials having elastic properties. In an alternative embodiment, the entirety of device frame 114 may be formed from a bioabsorbable material, such as Poly-L-lactic acid (PLLA), Poly(glycolic acid) (PGA), Copolyesters of poly(e-caprolactone) (PCL), poly(lactic-co-glycolic acid) (PLGA), Poly(D,L-lactide-co-glycolide) (PDLGA), poly (L-co-D,L lactic acid) (PLDLA), or polycaprolactone (PCL).

In one embodiment, patch 116 is formed from a bioabsorbable polymer. The bioabsorbable polymer may include, for example, Poly-L-lactic acid (PLLA), Poly(glycolic acid) (PGA), Copolyesters of poly(e-caprolactone) (PCL), poly (lactic-co-glycolic acid) (PLGA), Poly(D,L-lactide-co-glycolide) (PDLGA), poly (L-co-D,L lactic acid) (PLDLA), polycaprolactone (PCL), Trimethylene carbonate (TMC), Poly(d-diozanone) (PPDO), and combinations of various polymers. Additionally or alternatively, the biomaterial patch is formed from another polymer. The polymer may include, for example, steralloy, tecothane, chronoprene, PET (Dacron™), polyester, polypropylene, polyethylene, HDPE, Pebax™, nylon, PTFE, polyolefins, and ePTFE. In other embodiments, patch 116 may be formed from a tissue, such as pericardial tissues. The tissues may be derived from, for example, porcine, bovine, equine, and/or collagen matrices.

Figure 15:
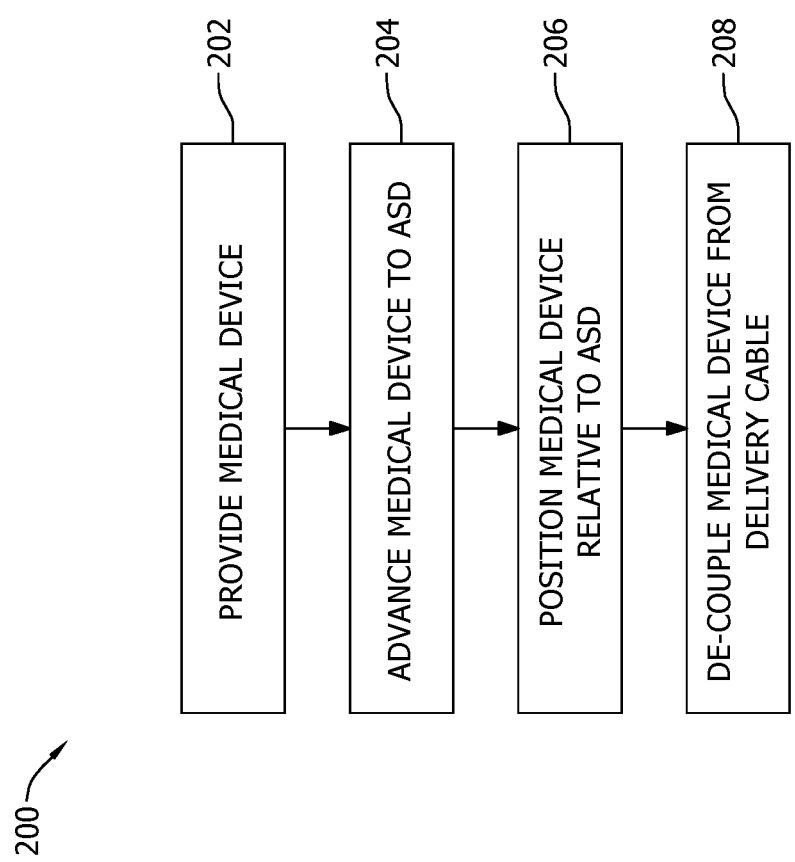
FIG. 15 is a flow diagram of a method of occluding a target site within a patient's vascular system using a medical device in accordance with the present disclosure.

Turning now to FIG. 15 a flow diagram of an exemplary method 200 of using medical device 112/150 to occlude an ASD in a patient is shown. In the exemplary embodiment, method 200 includes providing 202 a medical device. As described herein, the medical device includes a frame having proximal and distal ends, the frame comprising a proximal disc at the proximal end, a distal disc at the distal end, and a connecting segment extending between the proximal end and the distal end and connecting the proximal and distal discs, wherein each of the proximal and distal discs comprise a respective plurality of lobes, wherein each lobe is defined by a peripheral strut, and at least one patch, wherein the at least one patch is coupled to at least one of the proximal and distal discs of the frame.

Method 200 also includes advancing 204 the medical device to the ASD using a delivery system including a catheter and a delivery cable, positioning 206 the medical device relative to the ASD to occlude blood flow, and de-coupling 208 the medical device from the delivery cable to deploy the medical device.

Method 200 may include additional, alternative, and/or fewer steps, including those described herein. For example, in some embodiments, positioning 206 the medical device relative to the ASD includes placing the distal disc of the medical device on the left atrial side of the ASD and the proximal disc on the right atrial side of the ASD.

Additionally, de-coupling 208 the medical device from the delivery cable includes medical device transitioning from the constricted configuration adopted for delivery from a catheter to the preset expanded configuration.

While embodiments of the present disclosure have been described, it should be understood that various changes, adaptations and modifications may be made therein without departing from the spirit of the disclosure and the scope of the appended claims. Further, all directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. It is intended that all matter contained in the above description or shown in the accompanying drawings shall be interpreted as illustrative only and not limiting. Changes in detail or structure may be made without departing from the spirit of the disclosure as defined in the appended claims.

Many modifications and other embodiments of the disclosure set forth herein will come to mind to one skilled in the art to which this disclosure pertains having the benefit of the teachings presented in the foregoing descriptions and the associated drawings. Therefore, it is to be understood that the disclosure is not to be limited to the specific embodiments described and that modifications and other embodiments are intended to be included within the scope of the appended claims. Although specific terms are employed herein, they are used in a generic and descriptive sense only and not for purposes of limitation.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. A medical device for treating a target site comprising:
   a frame having proximal and distal ends, the frame comprising a proximal disc at the proximal end, a distal disc at the distal end, and a connecting segment extending between the proximal end and the distal end and connecting the proximal and distal discs, wherein each of the proximal and distal discs comprise a respective plurality of lobes, wherein each lobe is defined by a peripheral strut; and
   at least one patch, wherein the at least one patch is coupled to at least one of the proximal and distal discs of the frame.

2. The medical device of claim 1, wherein each lobe extends outwardly from the connecting segment to an exterior edge to define a loop.

3. The medical device of claim 1, wherein each lobe is circular or teardrop shaped in configuration.

4. The medical device of claim 1, wherein the frame comprises a tubular member integrally defining the proximal disc, the distal disc, and the connecting segment.

5. The medical device of claim 4, wherein the tubular member comprises the plurality of peripheral struts respectively defining the plurality of lobes.

6. The medical device of claim 1, wherein the at least one patch comprises a plurality of bioabsorbable patches respectively coupled to the plurality of lobes.

7. The medical device of claim 6, wherein each bioabsorbable patch is coupled to the corresponding lobe by one or more sutures.

8. The medical device of claim 1, wherein the at least one patch comprises a first patch positioned within the proximal disc and a second patch positioned within the distal disc.

9. The medical device of claim 1, wherein the medical device transitions from a constricted configuration to an expanded configuration when deployed at the target site.

10. The medical device of claim 9, wherein the medical device transitions from the constricted configuration to the expanded configuration in response to an axially compressive force.

11. The medical device of claim 1, wherein the proximal disc comprises at least two layers, each layer comprising a respective subset of the plurality of lobes of the proximal disc.

12. The medical device of claim 1, wherein the frame comprises a shape-memory material.

13. The medical device of claim 1, wherein the frame comprises a non-shape-memory material.

14. The medical device of claim 1, wherein the at least one patch comprises a bioabsorbable material.

15. A delivery system for deploying a medical device to a target site, the delivery system comprising:
    a medical device comprising:
        a frame and at least one patch, the frame having proximal and distal ends, the frame comprising a proximal disc at the proximal end, a distal disc at the distal end, and a connecting segment extending between the proximal end and the distal end and connecting the proximal and distal discs, wherein each of the proximal and distal discs comprise a respective plurality of lobes, wherein each lobe is defined by a peripheral strut, and wherein the at least one patch is coupled to at least one of the proximal and distal discs of the frame; and
    a delivery device comprising:
        a delivery catheter;
        a delivery cable within the delivery catheter and translatable with respect to the delivery catheter; and
        a coupling member configured to couple the medical device to the delivery cable for facilitating at least one of deployment of the medical device at the target site.

16. The delivery system of claim 15, the delivery device further comprising a pull wire coupled to the distal end of the medical device and a push wire coupled to the proximal end of the medical device.

17. The delivery system of claim 15, wherein the at least one patch comprises a bioabsorbable material.

18. A method for closing an atrial septal defect (ASD), the method comprising:
    providing medical device comprising a frame and at least one cover, the frame having proximal and distal ends, the frame comprising a proximal disc at the proximal end, a distal disc at the distal end, and a connecting segment extending between the proximal end and the distal end and connecting the proximal and distal discs, wherein each of the proximal and distal discs comprise a respective plurality of lobes, wherein each lobe is defined by a peripheral strut, and wherein the at least one patch is coupled to at least one of the proximal and distal discs of the frame;
    advancing the medical device to the ASD using a delivery system including a catheter and a delivery cable;

positioning the medical device relative to the ASD to occlude blood flow; and de-coupling the medical device from the delivery cable to deploy the medical device.

19. The method of claim 18, wherein said positioning the medical device comprises placing the distal disc of the medical device on the left atrial side of the ASD and the proximal disc on the right atrial side of the ASD.

20. The method of claim 18, wherein said de-coupling the medical device comprises transitioning the medical device from a constricted configuration adopted for delivery through the catheter to an expanded configuration.

* * * * *